US008642800B2

(12) United States Patent  
Jephcote et al.

(10) Patent No.: US 8,642,800 B2
(45) Date of Patent: Feb. 4, 2014

(54) PREPARATION METHOD OF ACYLBENZENES

(75) Inventors: Vincent John Jephcote, Aryshire (GB); Hongyan Shen, Shanghai (CN)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/146,522

(22) PCT Filed: Feb. 22, 2010

(86) PCT No.: PCT/CN2010/000227
§ 371 (c)(1),
(2), (4) Date: Oct. 11, 2011

(87) PCT Pub. No.: WO2010/099693
PCT Pub. Date: Sep. 10, 2010

(65) Prior Publication Data
US 2012/0022284 A1  Jan. 26, 2012

(30) Foreign Application Priority Data

Mar. 4, 2009  (CN) .......................... 2009 1 0118751

(51) Int. Cl.
*C07C 69/16* (2006.01)
(52) U.S. Cl.
USPC ....................................................... 560/144
(58) Field of Classification Search
CPC .................................................. C07C 67/293
See application file for complete search history.

(56) References Cited

FOREIGN PATENT DOCUMENTS

| JP | 55-130934 | 10/1980 |
| JP | 2007-504191 | 3/2007 |
| JP | 2009-298715 | 12/2009 |

OTHER PUBLICATIONS

Scheiper et al, Journal of Organic Chemistry, Selective Iron-Catalyzed Cross-Coupling Reactions of Grignard Reagents with Enol Triflates, Acid Chlorides, and Dichloroarenes, 2004, 69, pp. 3943-3949.*
White et al, Basic Energy Sciences Advisory Committee Subpanel Workshop Report, Opportunities for Catalysis in the 21st Century, 2002, pp. 1-47.*
Lu Zhenrong et al., "Study on Synthesis of 3,5-Dihydroxyacetophenone", *Shanxi Chemical Industry*, Mar. 1998, No. 1, pp. 30-31 (with an English abstract).
V. Fiandenese et al., "Iron Catalyzed Cross-Coupling Reactions of Acyl Chlorides with Grignard Reagents, A Mild, General, and Convenient Synthesis of Aliphatic and Aromatic Ketones", *Tetrahedron Letters*, vol. 25, No. 42, 1984, pp. 4805-4808.
Von A. Sous et al., "Synthese von Radioaktiv Markiertem Reproterol-hydrochlorid", *Arzneimittel-Forschung, Drug Research*, vol. 27, No. 1a, 1977, pp. 35-36.
R. Huls et al. Preparation de quelques dihydroxy-3-5 acylophenones au moyen de derives organoeadmiques, Bull. Soc. Chim. Belg., 65, pp. 596-602, (1956).
International Search Report for PCT/CN2010/000227, dated May 27, 2010.
Zhenrong et al., "Study on Synthesis of 3,5-Dihydroxyacetopheone", *Shanxi Chemical Industry*, Mar. 1998, No. 1, pp. 30-31.
Huls et al., "Preparation de Quelques Dihydroxy-3,5 Acylophenones au Moyen de Derives Organocadmiques", *Bull. Soc. Chim. Belg.* 1956, vol. 65, pp. 596-602.
Fiandenese et al., "Iron Catalyzed Cross-coupling Reactions of Acyl Chlorides with Grignard Reagents, A Mild, General, and Convenient Synthesis of Aliphatic and Aromatic Ketones", *Tetrahedron Letters*, 1984, vol. 25, No. 42, pp. 4805-4808.
Sous et al., "Synthese von Radioaktiv Markiertem Reproterol-hydrochlorid", *Arzneimittel-Forschung*, 1977, vol. 27, No. 1a, pp. 35-36.
Guiso et al, "A new efficient reservatrol synthesis," Tetrahedron Letters 43 (2002), pp. 597-598, Italy.

* cited by examiner

*Primary Examiner* — Paul A Zucker
(74) *Attorney, Agent, or Firm* — Nixon & Vanderhye P.C.

(57) ABSTRACT

A process for the production of acylbenzenes, comprising reacting diacetoxybenzoyl chloride with a Grignard reagent in the presence of an iron-containing catalyst. The acylbenzenes are useful intermediates in a multistep process for the preparation of resveratrol.

5 Claims, No Drawings

PREPARATION METHOD OF ACYLBENZENES

This application is the U.S. national phase of International Application No. PCT/CN2010/000227 filed 22 Feb. 2010 which designated the U.S. and claims priority to CN Patent Application No. 200910118751.2 filed 4 Mar. 2009, the entire contents of each of which are hereby incorporated by reference.

TECHNICAL FIELD

The present invention relates to a multistep process for the manufacture of resveratrol. Particularly, the present invention relates to a process for the manufacture of 3,5-diacetoxyacylbenzenes which are represented structurally by the formula

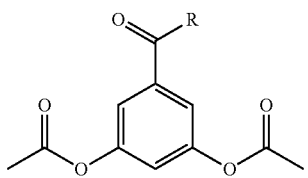

(I)

and their use as intermediates in the preparation of resveratrol, wherein R represents a lower alkyl group with 1-10 carbon atoms.

BACKGROUND OF THE INVENTION

Resveratrol with systematic name of 3,4',5-trihydroxystilbene is a known, naturally occurring compound which has gained much interest during the last years in view of its valuable biological properties and pharmacological effects. Resveratrol has been reported to exhibit many therapeutic as well as disease preventive effects including being considered as the reason of the so-called "French Paradox". The French Paradox is the fact that in people living on a Mediterranean diet, containing high levels of fat and alcohol, an increase to be expected in cancer and heart diseases is not observed. Effects of resveratrol in various cellular and animal assays have been shown, e.g., to inhibit not only skin tumors and leukemia but also platelet aggregation and coagulation. In addition, resveratrol has been shown to be a vasorelaxant, an antimicrobial and fungicidal agent. Recently, data has been published demonstrating that resveratrol is capable of extending the longevity of mice fed a high fat diet.

There have been numerous publications on the synthesis of resveratrol. Chinese patent No.: ZL 200480025470 describes a process for the preparation of resveratrol starting from 3, 5-diacetoxyacetophenone. J. Liu gave an overview of synthesis of resveratrol on August 2007 (see J. Liu, Synthesis of resveratrol and its analogs, phase-transfer catalysed asymmetric glycolate aldol reactions, and total synthesis of 8, 9-methylamido-geldanamycin, Brigham, Department of Chemistry and Biochemistry, Brigham Young University, August 2007). This synthesis process used 3,5-diacetoxyacetophenone. As described therein, "3,5-diacetoxybenzoyl-chlorides were not explored previously (see line 1 on page 17)". Based on the inventor's knowledge, currently there is no known publication regarding the process for producing 3,5-diacetoxyacetophenone.

Zhenrong Lu et al. describes a method for synthesis of 3,5-dihydroxyacetophenone by esterification, chlorizating, methylating starting from 3,5-dihydroxybenzoic acid as material, but the overall yield is only 41%. (see Lu, Zhenrong, et al, Study on synthesis of 3,5-dihydroxyacetophenone; *Shanxi Chemistry and Industry*, March 1998, pages 12-13).

Another known synthesis method involves coupling acyl chlorides with Grignard reagents at room temperature in the presence of the catalyst of tris(acetylacetonate)iron(III), Fe(AcAc)$_3$. But production of 3,5-diacetoxy-acetophenone is not disclosed (see V. Fiandanese, et al, Iron catalyzed cross-coupling reactions of acyl chlorides with Grignard reagents. A mild, general and convenient synthesis of aliphatic and aromatic ketones. *Tetrahedron Letters*, Vol. 25, No. 42, pp 4805-4808, 1984).

Therefore, considering the importance of multistep synthesis of resveratrol, there is a need in the industry to provide a process for the production of 3,5-diacetoxyacetophenone.

SUMMARY OF THE INVENTION

Therefore, based upon vast study and investigations, and proved by experimental data, the inventors of the present invention successfully developed a new process for producing 3,5-diacetoxyacetophenone and its analogues. Therefore the objective of this invention is to provide a process for the preparation of a 3,5-diacetoxyacetophenone and its analogues, comprising the steps of (1) conducting acylation of 3,5-dihydroxybenzoic acid with an anhydride under catalysis of pyridine to give 3,5-diacyloxybenzoic acid, preferably with acetic anhydride to form 3,5-diacetoxybenzoic acid; (2) chlorinating 3,5-diacyloxybenzoic acid (preferably 3,5-diacetoxybenzoic acid) with thionyl chloride in methylene chloride to get the diacyloxybenzoyl chloride (preferably diacetoxybenzoyl chloride); and (3) reacting the diacyloxybenzoyl chloride (preferably diacetoxybenzoyl chloride) with a Grignard reagent to obtain 3,5-diacetoxy-acetophenone and its analogues, in the presence of iron-containing catalyst.

The multi-step reaction for the preparation of resveratrol intermediates is illustrated in the following reaction scheme wherein the phenolic hydroxyl groups are protected with acetyl groups.

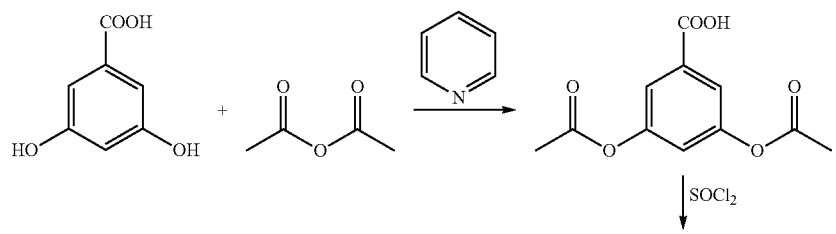

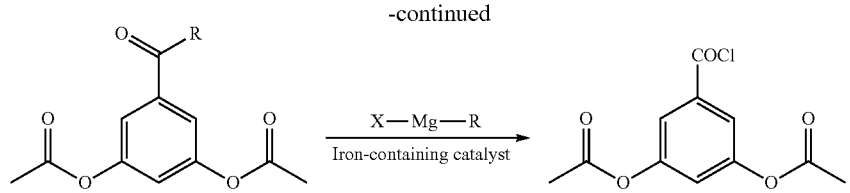

Therefore, the present invention provides a process for the preparation of 3,5-diacetoxyacylbenzenes represented by the following formula

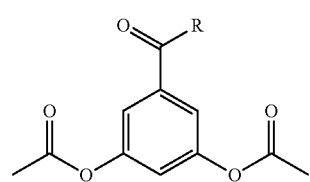

(I)

wherein R represents a lower alkyl group with 1-10 carbon atoms, comprising reacting diacetoxybenzoyl chloride with a Grignard reagent in the presence of an iron-containing catalyst. Preferably, the iron-containing catalyst is selected from the group consisting of $Fe(AcAc)_3$, iron phthalocyanine chloride, tris(dibenzoylmethanato)iron, tris(hexafluoroacetylacetonato)iron, anhydrous ferric chloride, ferrocene, iron trifluoroacetylacetonate and iron tetraphenylporphine chloride.

Apart from acetyl which is preferred as protecting groups for the phenolic hydroxyl groups in 3- and 5-position of the benzene ring also other acyl residues can be used such as propionyl, isobutyryl and benzoyl groups. The phenolic OH groups can also be protected with benzyl groups.

The Grignard reaction is carried out in a manner known per se, i.e. with a Grignard reagent of formula X—Mg—R, wherein X is selected from Cl, Br or I, and R is a lower-alkyl group with 1-10 carbon atoms. Preferably X is Cl or Br and R is methyl or ethyl, and most preferably X is Cl and R is methyl. The preferred solvent for the present reaction is tetrahydrofuran (THF).

The reaction of the present invention is carried out at a temperature from about $-70°$ C. to about $40°$ C., preferably at a temperature from about $-40°$ C. to about $25°$ C. One of ordinary skill in the art will understand that the lower the reaction temperature is, the higher a yield can be expected.

The reaction mixture useful in the invention is prepared according to well-known methods. The reaction mixture can be quenched with various quenching agents. The reaction mixture of the invention is preferably quenched with saturated $NH_4Cl$ aqueous solution or dilutes HCl aqueous solution.

In the reaction mixture, the molar ratio of Grignard reagent and acid chloride is from about 1:10 to about 2:1, preferably from 1:2 to 1:1.

In the reaction the molar ratio of the iron-containing catalyst and the acid chloride is from about 0.5% to about 10% preferably from 1% to 5%, and even more preferably about 3%.

DETAILED DESCRIPTION OF THE INVENTION

The present invention is illustrated by the following examples. One skilled in the art will understand that the below examples are only for the purpose of illustration, while the scope of the present invention is defined by the claims of present application.

EXAMPLE 1

Step 1: Acetoxybenzoic Acid

A 100 ml three-necked flask with magnetic stirrer, thermometer and condenser was charged with 30 g (0.195 mol) of 3,5-dihydroxybenzoic acid, 47 ml (0.497 mol) of acetic anhydride and 2.4 ml (29.8 mmol) of pyridine. The mixture was heated to $100°$ C. and kept under stirring for 3-4 hours then cooled down, poured into 400 ml of ice water and filtered. The filter cake was washed with ice water and dried at $45°$ C. under 1 mbar vacuum. 41 g of 3,5-diacetoxybenzoic acid as a white solid was obtained. The yield was 88.4%.

Step 2: Diacetoxybenzoyl Chloride

A 250 ml three-necked flask with magnetic stirrer, thermometer and condenser was charged with 15.4 g (64.7 mmol) of 3,5-diacetoxybenzoic acid, 10 ml of thionyl chloride and 80 ml of $CH_2Cl_2$. The mixture was refluxed for 3-5 hours. Then the solvent and remaining thionyl chloride were distilled off. Fresh $CH_2Cl_2$ was added and distilled off again. The crude solid was dissolved in 120 ml toluene, and the solution was filtered. Evaporated the solvent out and dried the product at room temperature under 1 mbar. 16.3 g of 3,5-diacetoxybenzoyl chloride were obtained as a white solid. The yield was 98.2%.

Step 3: 3,5-Diacetoxy-acetophenone

Under nitrogen atmosphere a 100 ml three-necked flask with magnetic stirrer, thermo-meter, dropping funnel and condenser was charged with 2 g (7.8 mmol) of diacetoxybenzoyl chloride, and 15 ml of dry THF. 2.6 ml of methylmagnesium chloride (3M in THF) were added dropwise to the solution over a period of 20 minutes. The reaction mixture was kept under stirring for further 10 minutes at room temperature. The mixture was then quenched with aqueous ammonium chloride. After extraction of the mixture with ethyl acetate the extract was dried over $MgSO_4$ and concentrated. The residue was analyzed by GC. The yield was 27%.

EXAMPLE 2

Steps 1 and 2 were carried out under the same conditions as in Example 1.

Step 3: 3,5-Diacetoxy-acetophenone

Under nitrogen atmosphere a 100 ml three-necked flask with magnetic stirrer, thermo-meter, dropping funnel and condenser was charged with 2 g (7.8 mmol) of diacetoxybenzoyl chloride, 83 mg (3 mol % based on acid chloride) of $Fe(AcAc)_3$ and 15 ml of dry THF. 2.6 ml of methylmagnesium chloride (3M in THF) were added dropwise to the solution over a period of 20 minutes. The reaction mixture was kept under stirring for further 10 minutes at the temperature indicated in Table 1. The mixture was then quenched with aqueous ammonium chloride. After extraction of the mixture with ethyl acetate the extract was dried over MgSO$_4$ and concentrated. The residue was analyzed by GC. The results are listed in Table 1.

TABLE 1

| Entry No.: | Reaction Scale (acid chloride) | Reaction Temp. | Quenched with | GC Yield (before isolation) |
| --- | --- | --- | --- | --- |
| 1 | 2 g | R.T. | Saturated NH$_4$Cl aqueous solution | 60.9% |
| 2 | 2 g | −10° C. | Saturated NH$_4$Cl aqueous solution | 70.3% |
| 3 | 2 g | −10° C. | Dilute HCl aqueous solution | 70.9% |
| 4 | 2 g | −40° C. | Saturated NH$_4$Cl aqueous solution | 78.5% |
| 5 | 6 g | −40° C. | Saturated NH$_4$Cl aqueous solution | 73.7% |

EXAMPLE 3

Steps 1 and 2 were carried out under the same conditions as in Example 1.
Step 3: 3,5-Diacetoxyacetophenone
Under a nitrogen atmosphere a 100 ml three-necked flask with magnetic stirrer, thermo-meter, dropping funnel and condenser was charged with 2 g (7.8 mmol) of diacetoxybenzoyl chloride, 141 mg (3 mol % based on acid chloride) of iron phthalocyanine chloride and 15 ml of dry THF. 2.6 ml of methylmagnesium chloride (3M in THF) were added dropwise to the solution over a period of 20 minutes. The reaction mixture was kept under stirring for further 10 minutes at −15° C. The mixture was then quenched with aqueous ammonium chloride. After extraction of the mixture with ethyl acetate the extract was dried over MgSO$_4$ and concentrated. The residue was analyzed by GC. The yield was 82.1%.

EXAMPLE 4

Steps 1 and 2 were carried out under the same condition as in Example 1.
Step 3: 3,5-Diacetoxy-acetophenone
Under a nitrogen atmosphere a 100 ml three-necked flask with magnetic stirrer, thermo-meter, dropping funnel and condenser was charged with 2 g (7.8 mmol) of diacetoxybenzoyl chloride, 169 mg (3 mol % based on acid chloride) of tris(dibenzoylmethanato) iron and 15 ml of dry THF. 2.6 ml of methylmagnesium chloride (3M in THF) were added dropwise to the solution over a period of 20 minutes. The reaction mixture was kept under stirring for further 10 minutes at −15° C. The mixture was then quenched with aqueous ammonium chloride. After extraction of the mixture with ethyl acetate the extract was dried over MgSO$_4$ and concentrated. The residue was analyzed by GC. The yield was 87.0%.

EXAMPLE 5

Steps 1 and 2 were carried out under the same conditions as in Example 1.
Step 3: 3,5-Diacetoxy-acetophenone
Under a nitrogen atmosphere a 100 ml three-necked flask with magnetic stirrer, thermo-meter, dropping funnel and condenser was charged with 2 g (7.8 mmol) of diacetoxybenzoyl chloride, 158 mg (3 mol % based on acid chloride) of tris(hexafluoroacetylacetonato)iron and 15 ml of dry THF. 2.6 ml of methylmagnesium chloride (3M in THF) were added dropwise to the solution over a period of 20 minutes. The reaction mixture was kept under stirring for further 10 minutes at −15° C. The mixture was then quenched with aqueous ammonium chloride. After extraction of the mixture with ethyl acetate, the extract was dried over MgSO$_4$ and concentrated. The residue was analyzed by GC. The yield was 77.5%.

EXAMPLE 6

Steps 1 and 2 were carried out under the same conditions as in Example 1.
Step 3: 3,5-Diacetoxy-acetophenone
Under nitrogen atmosphere a 100 ml three-necked flask with magnetic stirrer, thermo-meter, dropping funnel and condenser was charged with 2 g (7.8 mmol) of diacetoxybenzoyl chloride, 38 mg (3 mol % based on acid chloride) of anhydrous ferric chloride and 15 ml of dry THF. 2.6 ml of methylmagnesium chloride (3M in THF) were added dropwise to the solution over a period of 20 minutes. The reaction mixture was kept under stirring for further 10 minutes at −15° C. The mixture was then quenched with aqueous ammonium chloride. After extraction of the mixture with ethyl acetate the extract was dried over MgSO$_4$ and concentrated. The residue was analyzed by GC. The yield was 83.6%.

EXAMPLE 7

Steps 1 and 2 were carried out under the same conditions as in Example 1.
Step 3: 3,5-Diacetoxy-acetophenone
Under a nitrogen atmosphere a 100 ml three-necked flask with magnetic stirrer, thermo-meter, dropping funnel and condenser was charged with 2 g (7.8 mmol) of diacetoxybenzoyl chloride, 44 mg (3 mol % based on acid chloride) of ferrocene and 15 ml of dry THF. 2.6 ml of methylmagnesium chloride (3M in THF) were added dropwise to the solution over a period of 20 minutes. The reaction mixture was kept under stirring for further 10 minutes at −15° C. The mixture was then quenched with aqueous ammonium chloride. After extraction of the mixture with ethyl acetate the extract was dried over MgSO$_4$ and concentrated. The residue was analyzed by GC. The yield was 67.5%.

EXAMPLE 8

Steps 1 and 2 were carried out under the same conditions as in Example 1.
Step 3: 3,5-Diacetoxy-acetophenone
Under a nitrogen atmosphere a 100 ml three-necked flask with magnetic stirrer, thermo-meter, dropping funnel and condenser was charged with 2 g (7.8 mmol) of diacetoxybenzoyl chloride, 120.5 mg (3 mol % based on acid chloride) of iron trifluoroacetylacetonate and 15 ml of dry THF. 2.6 ml of methylmagnesium chloride (3M in THF) were added dropwise to the solution over a period of 20 minutes. The reaction mixture was kept under stirring for further 10 minutes at −15° C. The mixture was then quenched with aqueous ammonium chloride. After extraction of the mixture with ethyl acetate the extract was dried over MgSO$_4$ and concentrated. The residue was analyzed by GC. The yield was 87%.

The invention claimed is:
1. A process for the preparation of acylbenzenes represented by the following formula (I):

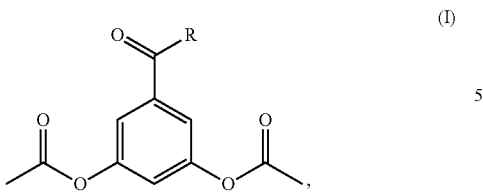

(I)

wherein

R represents a lower-alkyl group with 1-10 carbon atoms, the process comprising reacting diacetoxybenzoyl chloride with a Grignard reagent in the presence of an iron-containing catalyst at a temperature from −70° C. to 40° C., wherein the iron-containing catalyst is selected from the group consisting of iron phthalocyanine chloride, tris(dibenzoylmethanato)iron, tris(hexafluoroacetylacetonato)iron, anhydrous ferric chloride, ferrocene, iron trifluoroacetylacetonate and iron tetraphenylporphine chloride.

2. The process of claim 1, wherein the Grignard reagent is represented by the formula X—Mg—R, wherein X is Cl, Br or I and R is a lower-alkyl group with 1-10 carbon atoms.

3. The process of claim 1, wherein the reaction is carried out at a temperature of from about −40° C. to about 25° C.

4. The process of claim 1, wherein the molar ratio of Grignard reagent to the acid chloride is from about 1:10 to about 2:1.

5. The process of claim 1, wherein the molar ratio of the iron-containing catalyst to the acid chloride is from about 0.5% to about 10%.

* * * * *